United States Patent [19]
Sohn

[11] Patent Number: 5,762,599
[45] Date of Patent: Jun. 9, 1998

[54] MAGNETICALLY-COUPLED IMPLANTABLE MEDICAL DEVICES

[75] Inventor: Zev Sohn, Modiin, Israel

[73] Assignee: Influence Medical Technologies, Ltd., Herzlia B., Israel

[21] Appl. No.: 236,448

[22] Filed: May 2, 1994

[51] Int. Cl.⁶ ............................................. A61M 1/00
[52] U.S. Cl. ......................... 600/30; 600/16; 417/420
[58] Field of Search ............................ 600/16, 17, 29, 600/30; 623/3; 417/420

[56] References Cited

U.S. PATENT DOCUMENTS

| | | |
|---|---|---|
| 2,970,548 | 2/1961 | Berner . |
| 3,419,018 | 12/1968 | Plishner . |
| 3,503,400 | 3/1970 | Osthagen et al. . |
| 3,527,220 | 9/1970 | Summers . |
| 3,575,158 | 4/1971 | Summers . |
| 3,608,088 | 9/1971 | Dorman et al. . |
| 3,642,004 | 2/1972 | Osthagen et al. . |
| 3,647,324 | 3/1972 | Rafferty et al. . |
| 3,731,672 | 5/1973 | Loe . |
| 3,744,063 | 7/1973 | McWhorter et al. . |
| 3,749,098 | 7/1973 | De Bennetot . |
| 3,750,194 | 8/1973 | Summers . |
| 3,777,737 | 12/1973 | Bucalo ........................ 128/843 |
| 3,810,259 | 5/1974 | Summers . |
| 3,812,841 | 5/1974 | Isaacson . |
| 3,817,237 | 6/1974 | Bolduc ........................ 600/30 |
| 3,926,175 | 12/1975 | Allen et al. . |
| 3,939,821 | 2/1976 | Roth . |
| 4,024,855 | 5/1977 | Bucalo . |
| 4,360,007 | 11/1982 | Levy et al. . |
| 4,401,107 | 8/1983 | Haber et al. . |
| 4,419,985 | 12/1983 | Trick . |
| 4,551,862 | 11/1985 | Haber . |
| 4,552,128 | 11/1985 | Haber . |
| 4,571,749 | 2/1986 | Fischell . |
| 4,679,546 | 7/1987 | van Waalaijk van Doorn ....... 128/1 |
| 4,705,518 | 11/1987 | Baker et al. . |
| 4,731,083 | 3/1988 | Fischell . |
| 4,779,614 | 10/1988 | Moise . |
| 4,784,660 | 11/1988 | Fischell . |
| 4,850,963 | 7/1989 | Sparks et al. . |
| 4,865,588 | 9/1989 | Flinchbaugh ..................... 604/129 |
| 4,904,256 | 2/1990 | Yamaguchi . |
| 4,908,012 | 3/1990 | Moise et al. ..................... 600/16 |
| 4,944,722 | 7/1990 | Carriker et al. . |
| 4,968,294 | 11/1990 | Salama . |
| 4,969,474 | 11/1990 | Schwarz . |

(List continued on next page.)

FOREIGN PATENT DOCUMENTS 2251302  7/1975  France .

OTHER PUBLICATIONS

"A New Miniature Pump for the Treatment of Hydrocephalus", by George D. Summers and Ernest S. Matthews, Journal of the Association for the Advancement of Medical Instrumentation, May/Jun. 1967.

*Primary Examiner*—William E. Kamm
*Assistant Examiner*—Kennedy J. Schaetzle
*Attorney, Agent, or Firm*—Levisohn, Lerner, Berger & Langsam

[57] ABSTRACT

Medical apparatus includes an external drive magnet mounted for rotation externally of a subject's body, an implantable driven magnet configured and dimensioned to be implantable in the subject's body and mounted for rotation by magnetic coupling with the drive magnet and an implantable device mechanically coupled to the driven magnet to be driven thereby. The driven magnet is mountable for rotation in the subject's body about an axis of rotation which is not collinear with the axis of rotation of the external drive magnet such that the magnetic poles of the external drive magnet are magnetically coupled sequentially with the magnetic poles of the implanted driven magnet to rotate the implanted driven magnet, thereby providing flexibility in the location, design and dimensions of the implanted driven magnet, and in the speed and torque ratios between the two magnets.

76 Claims, 13 Drawing Sheets

U.S. PATENT DOCUMENTS

| | | |
|---|---|---|
| 4,994,019 | 2/1991 | Fernandez et al. . |
| 5,004,454 | 4/1991 | Beyar et al. . |
| 5,012,822 | 5/1991 | Schwarz . |
| 5,030,199 | 7/1991 | Barwick et al. . |
| 5,041,092 | 8/1991 | Barwick . |
| 5,092,844 | 3/1992 | Schwartz et al. ............... 604/151 |
| 5,097,848 | 3/1992 | Schwarz . |
| 5,112,306 | 5/1992 | Burton et al. . |
| 5,114,398 | 5/1992 | Trick et al. . |
| 5,114,412 | 5/1992 | Flinchbaugh ............... 604/247 |
| 5,140,999 | 8/1992 | Ardito . |
| 5,197,984 | 3/1993 | Kedem . |
| 5,211,546 | 5/1993 | Isaacson et al. ............... 417/356 |
| 5,326,344 | 7/1994 | Bramm et al. . |
| 5,366,506 | 11/1994 | Davis ............... 600/30 |
| 5,380,268 | 1/1995 | Wheeler ............... 600/30 |

FIG. I
PRIOR ART
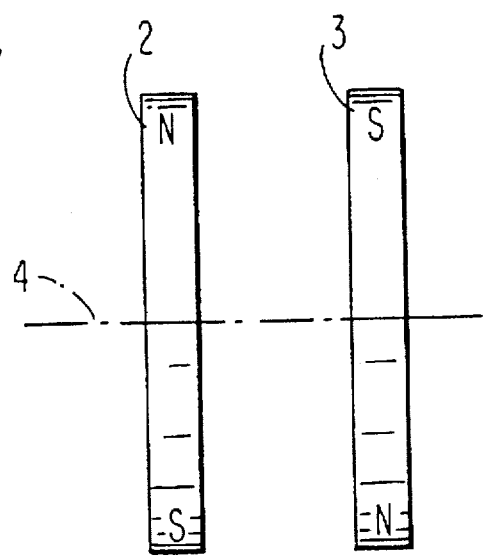
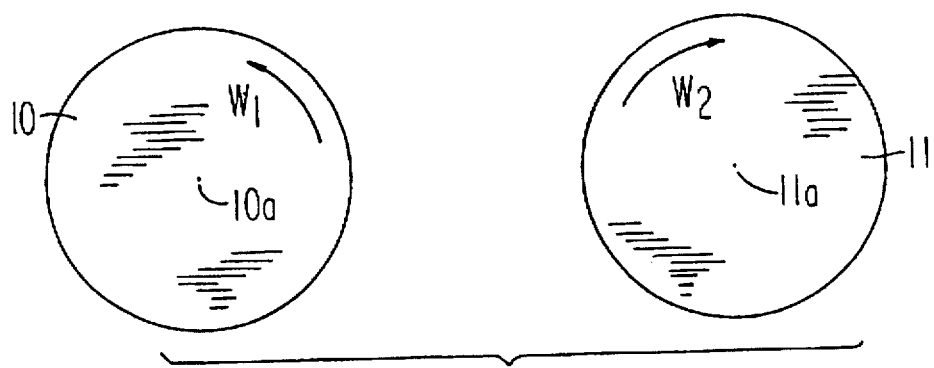
FIG. 2

MAGNETICALLY-COUPLED IMPLANTABLE MEDICAL DEVICES

FIELD AND BACKGROUND OF THE INVENTION

The present invention relates to medical apparatus, and particularly to medical devices adapted to be implanted into a subject's body and to be magnetically-coupled to an external drive magnet.

Medical apparatus is known comprising an external drive magnet mounted for rotation externally of a subject's body; an implantable driven magnet configured and dimensioned to be implantable in the subject's body and mounted for rotation by magnetic coupling with the drive magnet when the driven magnet is implanted in the subject's body and the drive magnet is rotated externally of the subject's body sufficiently close to the implanted driven magnet to be magnetically coupled thereto; and an implantable device mechanically coupled to the driven magnet to be driven thereby. Examples of such apparatus are described in U.S. Pat. Nos. 3,575,158 and 3,810,259, both relating to an implantable pump for controlling urine flow.

In such apparatus, the two magnets rotate about the same axis (i.e., the two rotary axes are collinear) such that the magnetic poles of the two magnets are continuously coupled by the magnetic field, and thus the operation of the two devices is analogous to a mechanical clutch.

OBJECTS AND BRIEF SUMMARY OF THE INVENTION

An object of the present invention is to provide medical apparatus of the foregoing type but having a number of advantages, as will be described more particularly below.

According to the present invention, there is provided medical apparatus of the foregoing type characterized in that the driven magnet is mountable for rotation in the subject's body about an axis of rotation which is not collinear with the axis of rotation of the external drive magnet such that the magnetic poles of the external drive magnet are magnetically coupled sequentially with the magnetic poles of the implanted driven magnet to rotate the implanted driven magnet, thereby providing flexibility in the location, design and dimensions of the implanted driven magnet, and in the speed and torque ratios between the two magnets.

As will be described more particularly below, the basic concept of the present invention, to implant the driven magnet about an axis for rotation which is not collinear with the axis of rotation of the external drive magnet such that the magnetic poles of the external drive magnet are magnetically coupled sequentially with the magnetic poles of the implanted driven magnet, produces an operation which is analogous to a "gear coupling", rather than a "clutch coupling" of the prior art. Such an operation permits a wide flexibility in the location, design and dimensions of the implanted driven magnet, and in the speed and torque ratios between the two magnets.

For example, where the implanted devices are to be used in a pump for urinary control as in the above-cited U.S. patents, the driven magnet may be implanted in the urethra of the subject and elongated in the direction of the urethra so as to increase the torque coupling between the drive and driven magnets. In addition, the implanted driven magnet may be provided with a smaller number of poles than the external drive magnet, which, although decreasing the torque ratio between the two magnets, correspondingly increases the speed of rotation of the implanted driven magnet analogous to the manner of increasing the speed ratio in a gear coupling according to the "gear ratio".

The high degree of flexibility in the location, design and dimensions of the implanted driven magnet provided by the above arrangement permits the device to be used in a large number of medical applications. Described below are implementations of the invention in the form of an artificial pump, e.g., for implanting into the urethra of a subject's body to pump urine from the bladder, for implantation into the aorta of a subject's body to pump blood (to assist a failing or recovering heart), or for implantation into another blood vessel of the subject's body, e.g., to aid blood circulation in an ischemic leg.

Other applications described below include an artificial valve to serve as an artificial sphincter, a generator for recharging an implanted battery, and a bone-stretching device.

Further features and advantages of the invention will be apparent from the description below.

BRIEF DESCRIPTION OF THE DRAWINGS

The invention is herein described, by way of example only, with reference to the accompanying drawings, wherein:

FIG. 1 illustrates an arrangement of a drive magnet and a driven magnet as used in the prior art, such as in the two above-cited patents;

FIGS. 2–5 illustrate different arrangements of drive magnets and driven magnets according to the present invention;

DESCRIPTION OF PREFERRED EMBODIMENTS

Figure 3:
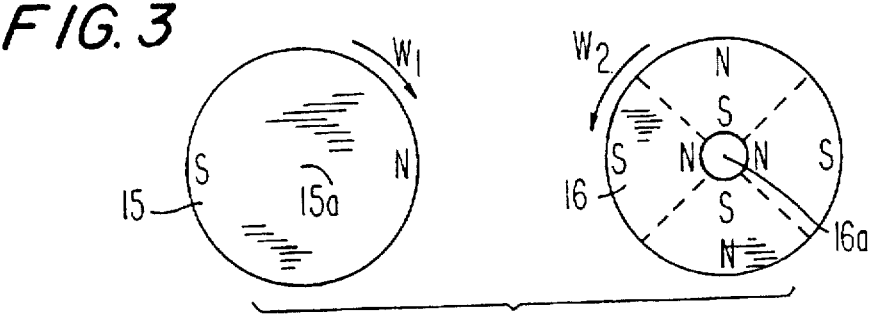

Reference is first made to FIG. 1 illustrating the prior art arrangement of a drive magnet 2 and a driven magnet 3 as previously used in implantable medical devices, such as in the above-cited two USA patents. In such a prior art arrangement, both the drive magnet 2 to be mounted for rotation externally of the subject's body, and the driven magnet 3 to be implanted into the subject's body, are mounted for rotation about the same axis 4; also, the magnetic poles of the two magnets are continuously coupled by the magnetic field. Therefore the driven magnet 3 is driven by the drive magnet 2 in a manner analogous to a mechanical clutch.

FIG. 2 illustrates one arrangement in accordance with the present invention, wherein the drive magnet 10 and driven magnet 11 have rotary axes 10a and 11a, respectively, which are not collinear; in this case, the two axes are in parallel spaced relation. The driven magnet 11 is adapted to be implanted into the subject's body, whereas the drive magnet 10 is adapted to be rotatably mounted externally of the subject's body. In such an arrangement, the magnetic poles of the external drive magnet 10 are magnetically coupled sequentially with the magnetic poles of the implanted driven magnet 11, analogous to a "gear" coupling rather than a "clutch" coupling as in the prior art arrangement of FIG. 1. This provides a high degree of flexibility in the location of the implanted driven magnet, and thereby in the design and dimensions of the implanted driven magnet, and also in the possible speed and torque ratios between the two magnets.

For example, FIG. 3 illustrates an arrangement similar to that of FIG. 2, but in this case the implanted driven magnet 15 has a smaller number of poles than the external drive magnet 16. The angular velocity between the two magnets is inversely proportional to the number of poles, whereas the torque transmission is directly proportional to the number of poles, analogous to a gear coupling. In this case, the implanted driven magnet 15 has one-half the number of poles as the external drive magnet 16, and will therefore rotate at twice the angular velocity, but will provide one-half the torque, as the external drive magnet.

In the arrangement of FIG. 3, the two magnets have parallel spaced axes of rotation 15a, 16a, respectively, as in FIG. 2. In the arrangement of FIGS. 2 and 3, the implanted driven magnet and the external drive magnet rotate in opposite directions.

Figure 4:
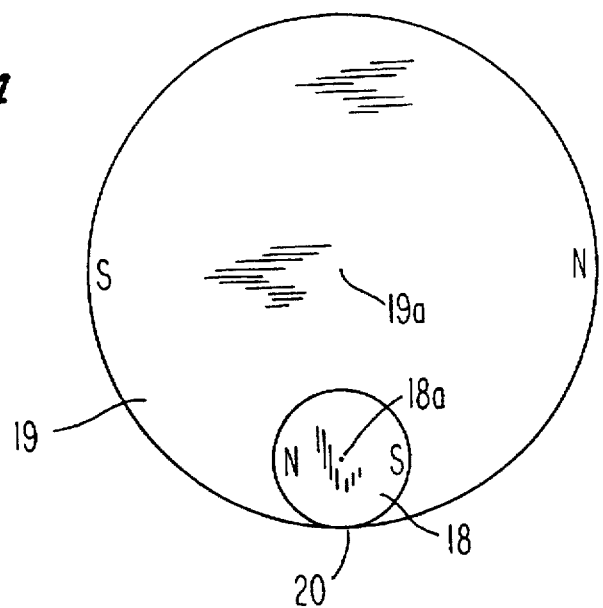

FIG. 4 illustrates a further arrangement wherein the drive magnet 19 and the driven magnet 18 also have spaced parallel axes of rotation 19a, 18a, respectively. In this case, however, the drive magnet 19 to be mounted externally of the subject's body has a larger diameter than in the implantable driven magnet 18, and its circumference is aligned with that of the implantable driven magnet 19 at one point 20 on both circumferences, analogous to a planetary gear or ring gear coupling. In the arrangement of FIG. 4, both magnets rotate in the same direction, analogous to a gear coupling of this type.

Figure 5:
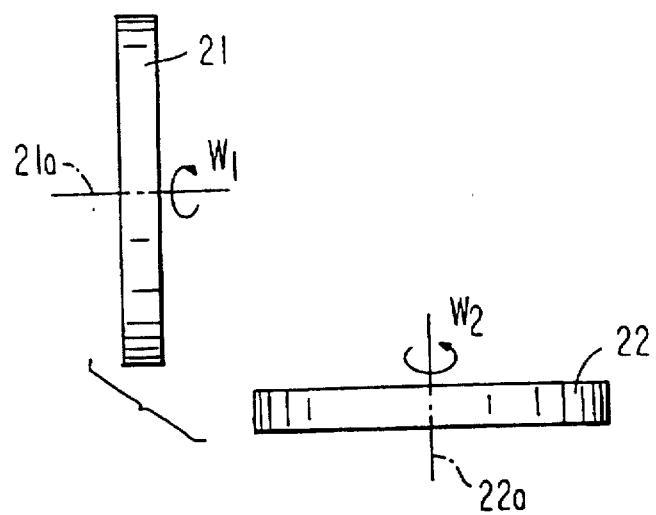
Figure 6:
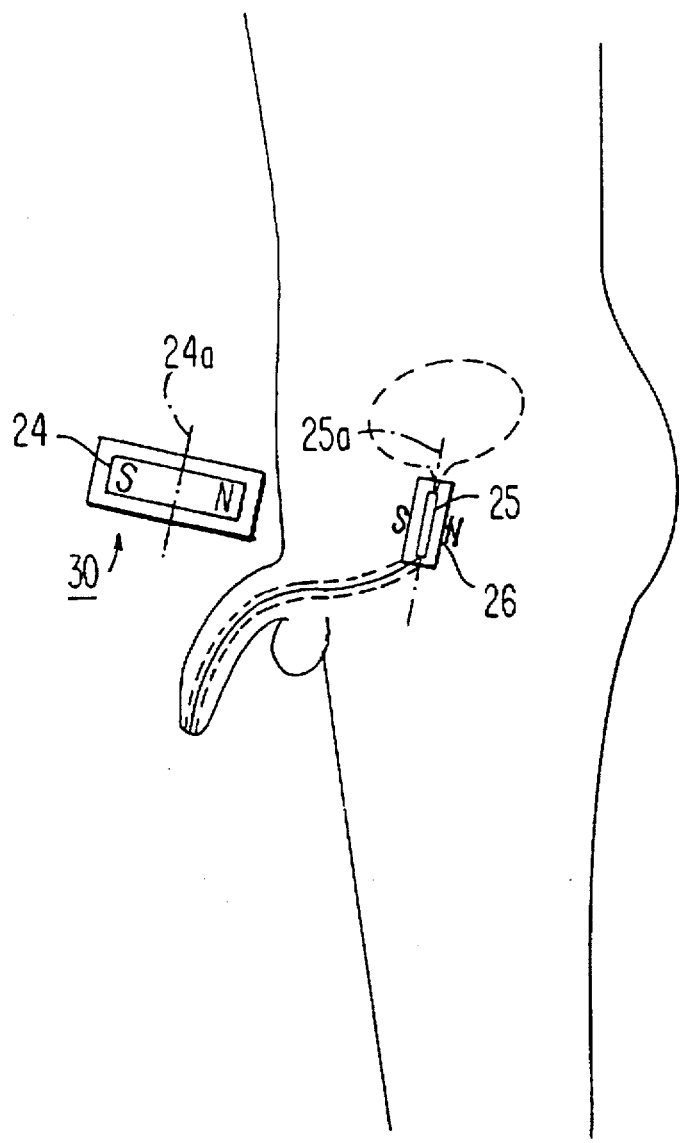
FIG. 6 illustrates an application of the invention as embodied in an intra-urethral pump in a male.

Providing a magnetic coupling between the drive and driven magnets analogous to a gear coupling, rather than to the prior art clutch coupling, enables the driven magnet to be implanted in an optimum position for the respective application. FIG. 5 illustrates an arrangement wherein the axes 21a, 22a, of the drive magnet 21 and driven magnet 22, respectively, are at right angles to each other analogous to a bevel gear coupling. FIG. 6 illustrates an arrangement wherein the rotary axes 24a, 25a, of the external drive magnet 24 and the implanted driven magnet 25 are oblique with respect to each other.

FIG. 6 illustrates a further advantage of the invention, in that it enables the driven magnet 25 not only to be implanted at an optimum location in the subject's body for the particular application, but also to be designed and dimensioned to provide the optimum torque for the respective application. In FIG. 6, the driven magnet 25 is part of a pump, generally designated 26, implanted in the urethra of the subject in order to promote the flow of urine from a non-contractile bladder, similar to the application in the above-cited U.S. patents. The gear-like system enables the urinary pump to be a small, highly-effective pump to be implanted intraurethrally in a non-surgical procedure. In contrast, the urinary pump described in the above-cited U.S. Pat. No. 4,575,158 requires a surgical operation and urethral incisions for the subcutaneous positioning of the magnetic coupling unit.

Figure 7:
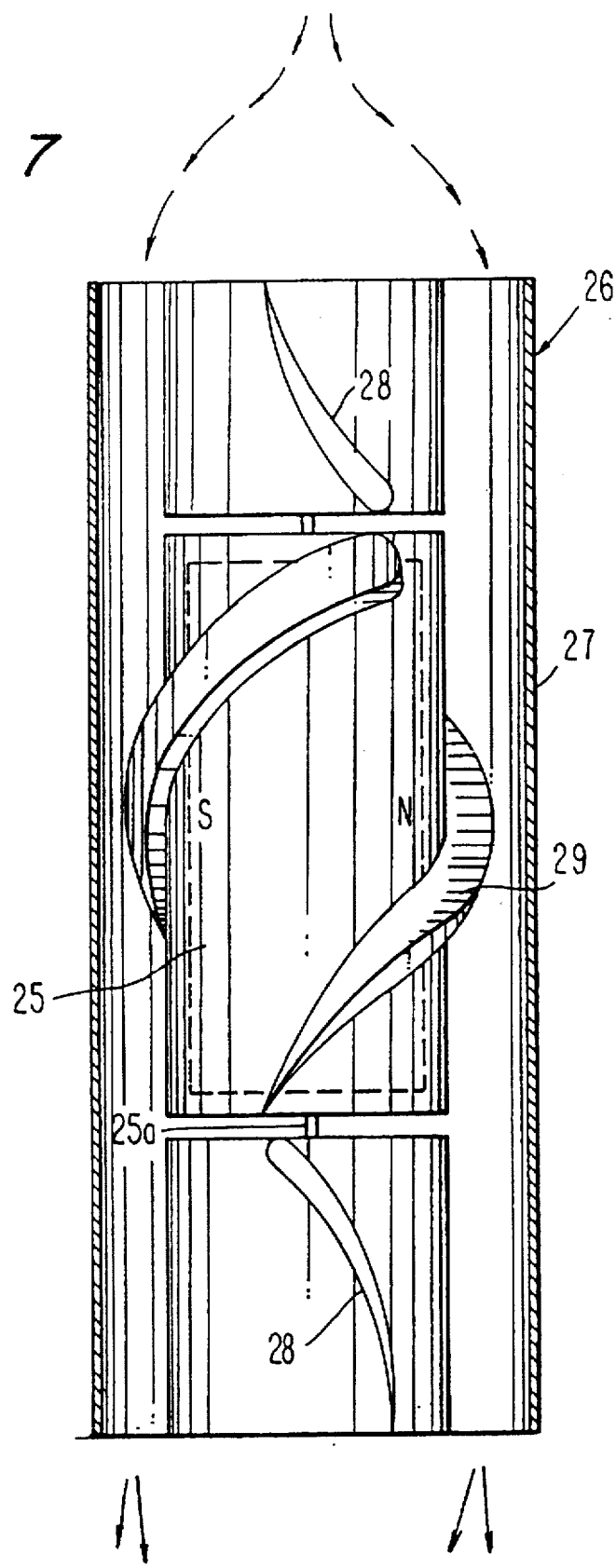
FIG. 7 illustrates the construction of the implanted pump of FIG. 6 including the implanted driven magnet rotating the pump.

FIG. 7 more particularly illustrates the construction of the intraurethrally implanted pump 26. It includes a tube 27 implanted in the urethra and formed at opposite ends with stationary vanes 28. The driven magnet 25 is rotatably mounted within tube 27 about rotary axis 25a and is formed on its outer circumference with impeller vanes 29 which are rotated by the rotation of the driven magnet 25.

It will be seen that implanting pump 26 at the location illustrated in FIG. 6 enables the driven magnet 25 to be optimally dimensioned for the particular application; that is, the driven magnet 25 is elongated in the direction of the urethra so as to increase the torque produced by its rotation as may be required for any particular application. The torque may also be increased by designing the driven magnet 25 with the appropriate number of magnetic poles with respect to that of the drive magnet 24 to provide a desired "gear ratio" for the particular application.

The external drive magnet 24 illustrated in FIG. 6 is part of a portable magnet drive unit, generally designated 30. This drive unit is more particularly illustrated in FIG. 8, wherein it will be seen it includes a housing 31 enclosing the drive magnet 24 and also enclosing a motor 32 driving magnet 24 about rotary axis 24a, and batteries 33 for energizing the electrical motor. The drive magnet 24 may be an integral part of the motor 32 providing the magnetic flux necessary to drive the motor. Housing 31 may be selectively shielded from magnet flux leakage.

Figure 8:
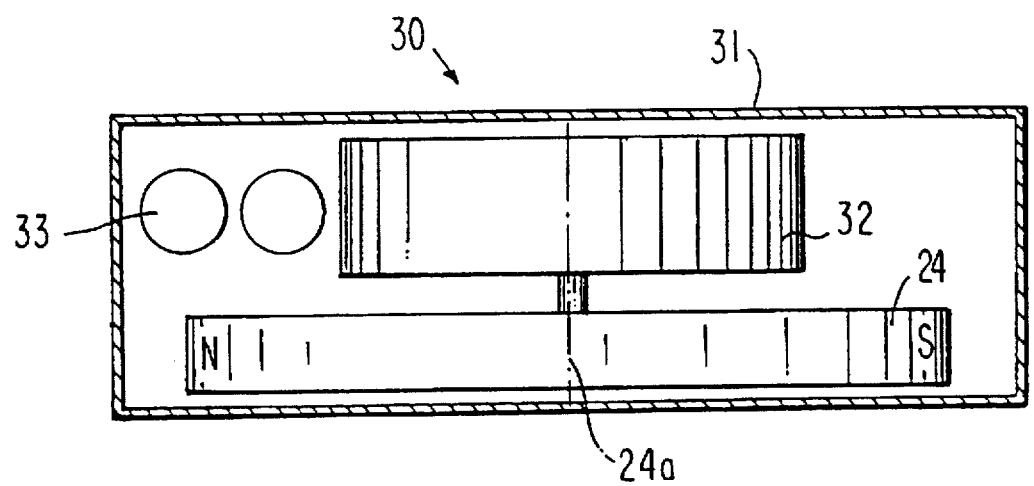
FIG. 8 illustrates the external drive magnet in the pump of FIG. 6.
Figure 9:
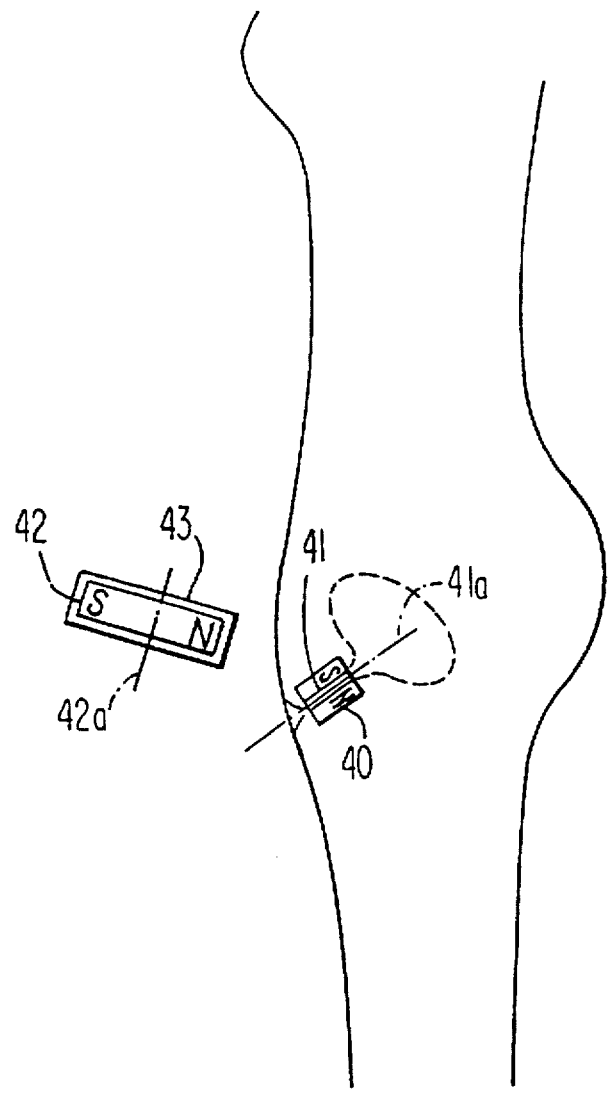
FIG. 9 illustrates an application of the invention in an intra-urethral pump in a female.

FIG. 9 illustrates a similar arrangement as in FIGS. 6–8, but wherein the artificial pump 40 is implanted in the urethra of a female. Thus, the implanted pump 40 includes a driven magnet 41 mounted for rotation about an axis 41a which is also oblique to the rotary axis 42a of the drive magnet 42 included within the portable unit 43 externally of the subject.

Figure 10:
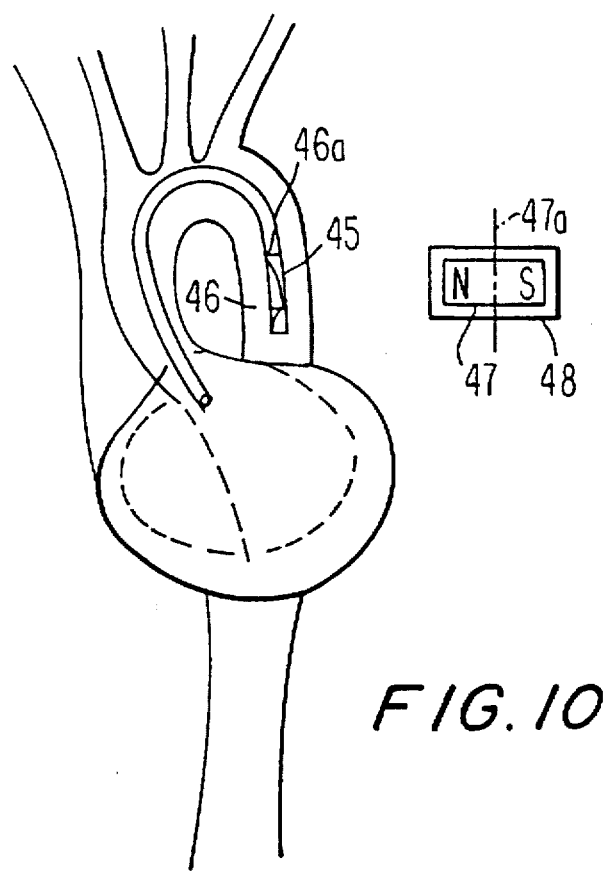
FIG. 10 illustrates an application of the invention as a heart-assist pump implanted in the aorta.

FIG. 10 illustrates the artificial pump 45 implanted in another tubular organ of the subject, in this case between the aorta and the left ventricle to assist the heart in pumping blood from the left ventricle towards the aorta. In this example, the driven magnet 46 within the implanted pump 45 has a rotary axis 46a which is oblique to the rotary axis 47a of the drive magnet 47 within the external drive unit 48.

Figure 11:
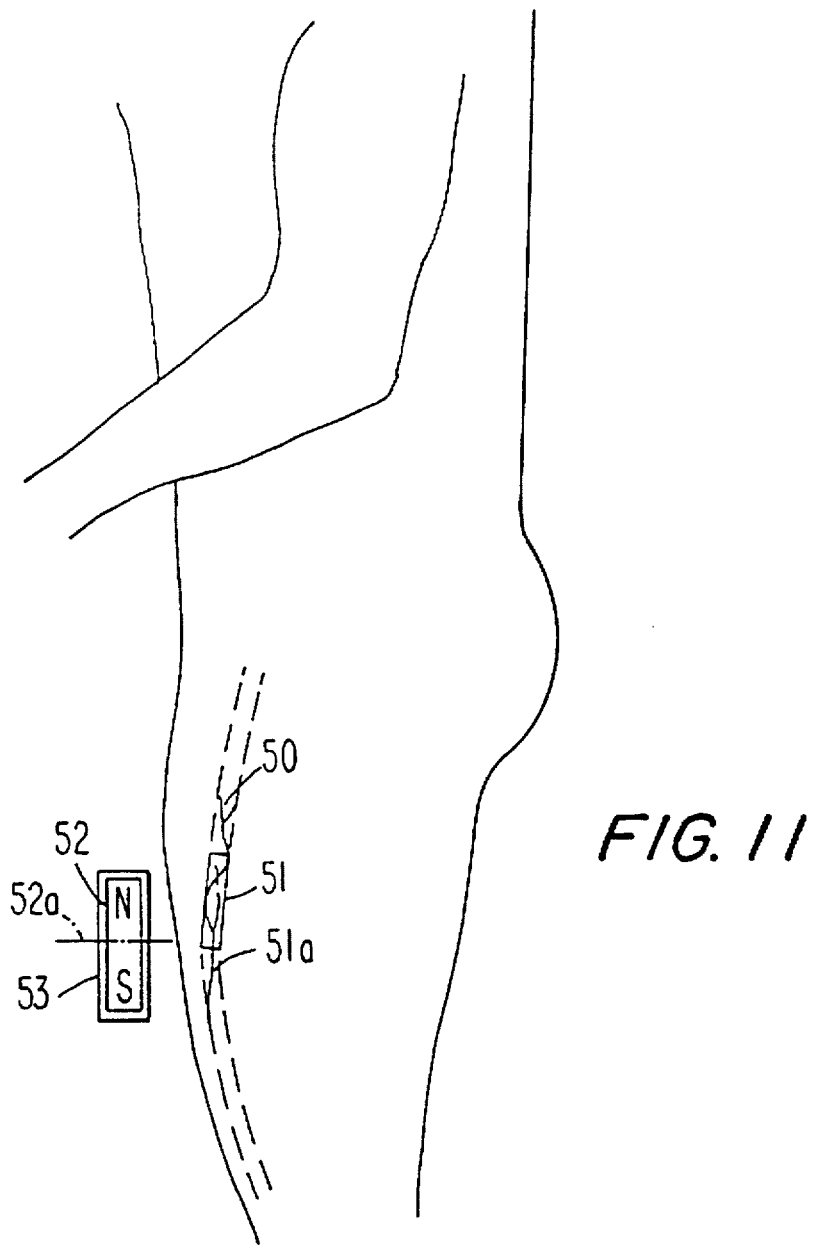
FIG. 11 illustrates an application of the invention as implanted in a vein to assist an ischemic leg.

FIG. 11 illustrates an artificial pump 50 implanted in another blood vessel, e.g., in a subject's leg to assist an ischemic leg. In this case, its driven magnet 51 is also mounted about a rotary axis 51a which is oblique to the rotary axis 52a of the drive magnet 52 within the external drive unit 53.

FIGS. 12–16 illustrate another application of the invention, wherein the driven magnet is included within an artificial valve to be implanted in the subject's body, e.g., to serve as an artificial sphincter.

Figure 12:
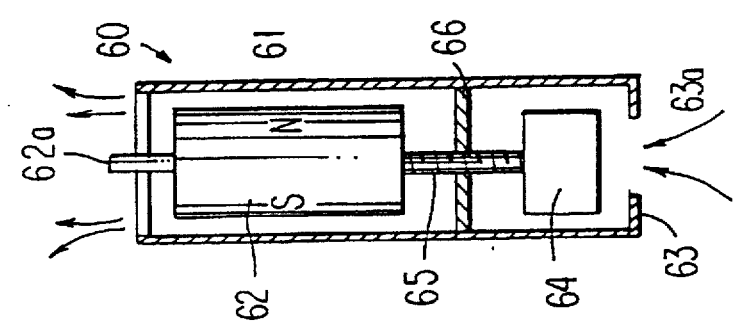
FIG. 12 illustrates the invention implemented in an intra-urethral valve to serve as an artificial sphincter.

The artificial valve illustrated in FIG. 12, and therein generally designated 60, includes a tubular housing 61 rotatably mounting the driven magnet 62 about a rotary axis 62a. The inlet end of housing 61 has a stop 63 formed with an inlet passageway 63a controlled by a plug 64. Plug 64 is axially movable towards and away from stop 63 by a screw 65 threadedly received within a fixed nut 66 and rotatable by the driven magnet 62. It will thus be seen that as the driven magnet 62 is rotated by the external drive magnet (not shown), screw 65 will be moved axially with respect to fixed nut 66, and will therefore move plug 64 axially towards and away from stop 63. FIG. 12 illustrates plug 64 in the open position of the artificial valve, i.e., spaced from stop 63.

Figure 13:
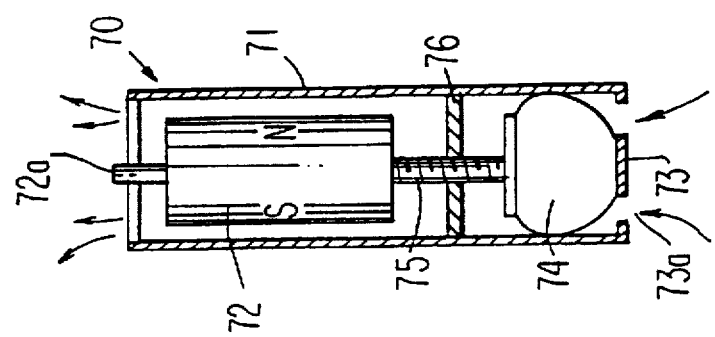

FIG. 13 illustrates another form of artificial valve, this time shown in the closed position. In this valve, the inlet end of its housing 71 has a stop 73 with an inlet passageway 73a. The plug 74 is made of an elastomeric material, such as rubber, and is stretched between the screw 75 and the stop 73. When the screw 75 rotates and moves axially towards the stop 73, the plug 74 is squeezed axially, and therefore expands radially until it engages the inner surface of tubular housing 71, thereby stopping the flow of fluid and closing the artificial valve.

Figure 14:
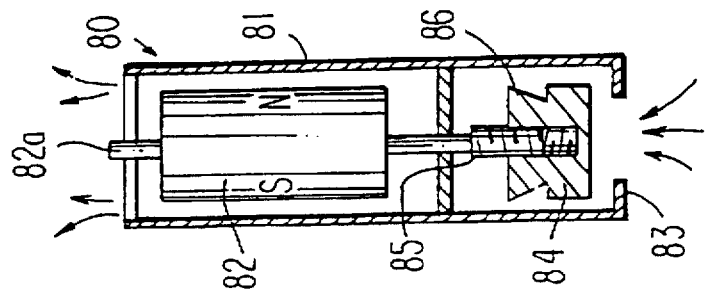
FIGS. 13–16b illustrate other constructions of an intra-urethral valve in accordance with the present invention.

FIG. 14 illustrates a construction similar to the artificial valve of FIG. 12, wherein a driven magnet 82 in a housing 81 rotates a screw 85. In this example, the screw 85 does not move axially. Instead, it drives the nut 86 and plug 84 against stop 83. In FIG. 14, the plug is illustrated in the open position away from stop 83.

Figure 15:
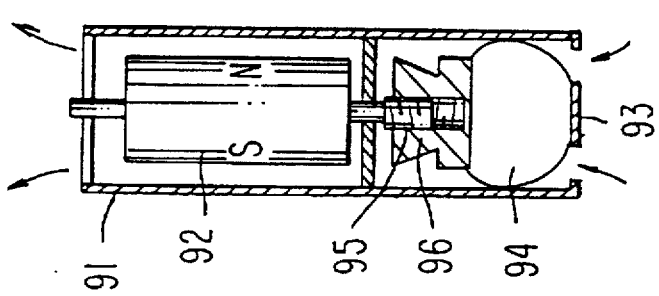

FIG. 15 illustrates a construction similar to the artificial valve of FIG. 13. In this construction, the screw 95 rotates but does not move axially; rather, it drives nut 96 axially. A plug 94 made of an elastomeric material is located between nut 96 and stop 93. The axial motion of nut 96 towards stop 93 expands the plug 94 radially until it engages the inner surface of tubular housing 91, thereby closing the artificial valve.

Figure 16B:
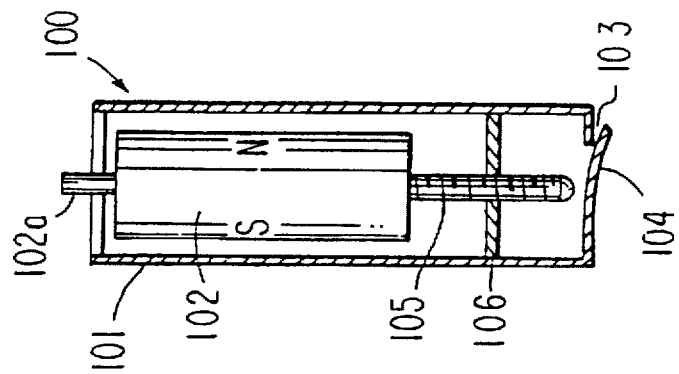
Figure 16A:
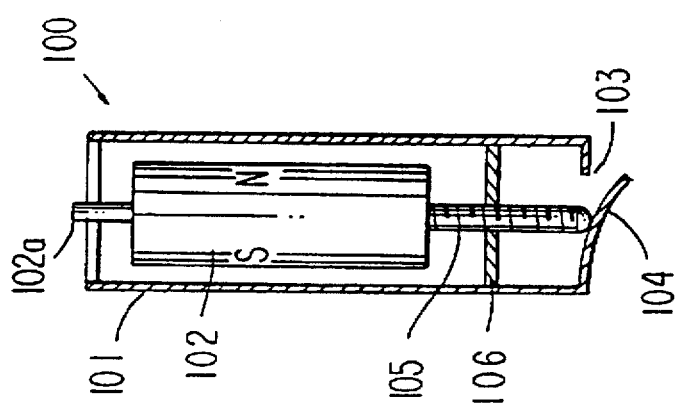

FIGS. 16a and 16b illustrate another type of artificial valve in the open position and closed position, respectively. In this valve construction, rotation of the driven magnet 102 moves a screw 105 axially with respect to a fixed nut 106. The inlet end of the housing 101 is covered with a flexible polymeric flap 104, which is pushed open by the axially moving screw 105. When the screw 105 moves axially away from the flap, the flap returns to its normally-closed position.

All the foregoing constructions as illustrated in FIGS. 12–16b can be designed to leak at a desired pressure, thereby also acting as pressure-release valves.

Figure 17:
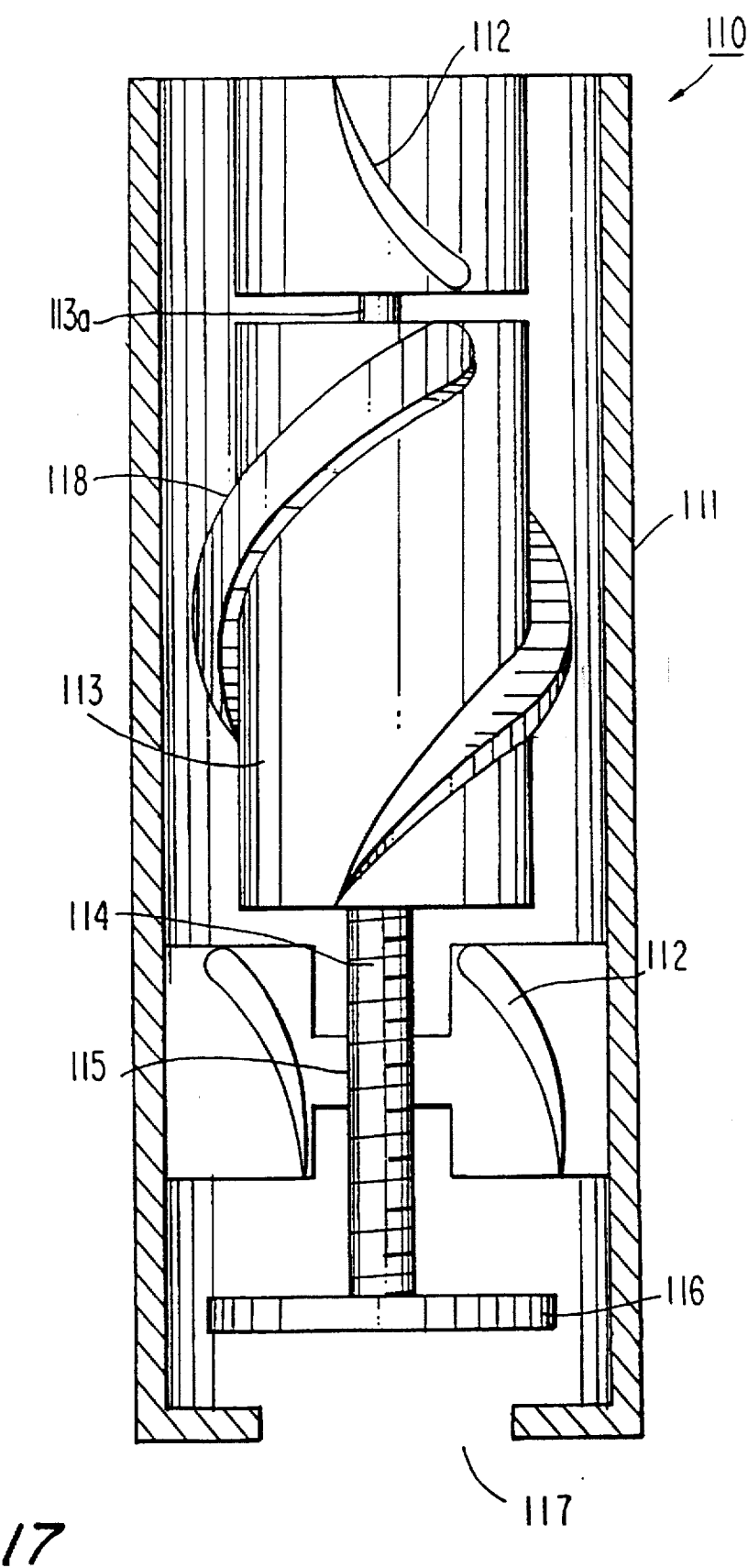
FIG. 17 illustrates a valve and pump combination constructed in accordance with the present invention.

FIG. 17 illustrates the invention embodied in a combined artificial pump and valve 110 to be implanted in a subject's body. This embodiment can be used as an intraurethral artificial sphincter and urine pump. It includes an outer tubular housing 111 to be implanted in the subject's body and formed with fixed blades 112 at its opposite ends. A driven magnet 113 is rotatably mounted within housing 111 about rotary axis 113a and rotates a screw 114 threadedly received within a fixed nut 115 such that the screw moves axially by the rotation of magnet 113. The end of the screw is formed with a plug or valve member 116 movable to open or close an opening 117 within the tubular housing 111. The outer surface of magnet 113 is formed with blades 118, such that the rotation of magnet 113 (by the external drive unit, not shown) not only pumps the liquid through housing 111, but also moves valve member 116 to its open or closed position with respect to opening 117.

It follows that any combination of the pump shown in FIG. 7 within any one of the valves shown in FIGS. 12–16 would perform in a manner similar to the combination in FIG. 17.

Another feature which can be included in the valves of FIGS. 12–16, or with the pump and valve of FIG. 17, is a limit of the axial movement of the screw or nut. Embodiments illustrating this feature are shown in FIGS. 18 and 19.

Figure 18:
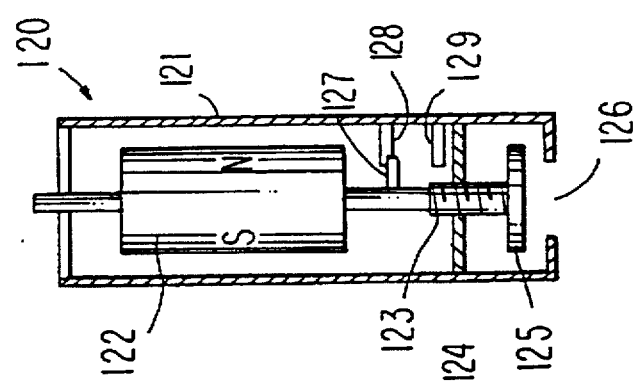

FIG. 18 illustrates an artificial valve, generally designated 120, including a tubular housing 121 enclosing a driven magnet 122 which rotates a screw 123 threaded within a nut 124 fixed to housing 121 for moving a valve member 125 to an open position or a closed position with respect to an opening 126. In this case, screw 123 is formed with a stop 127 which is engageable by two limit stops 128, 129 fixed to tube 121, in order to limit the movement of the valve member 125.

Figure 19:
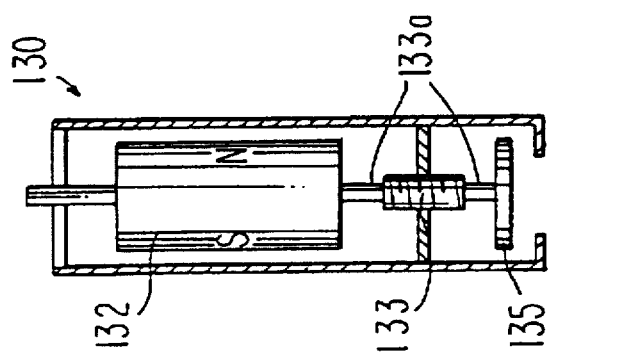
FIGS. 18 and 19 illustrate two further forms of valves constructed in accordance with the present invention with limited axial motion of the plug.

FIG. 19 illustrates a similar valve construction, except that the screw 133 is only partially threaded, as shown at 133a, to limit the movement of the valve member 135. This construction allows the driven magnet 132 to continue rotating even after the valve is completely opened or closed. This feature permits pumping to continue after a valve has been completely opened in the case of a combined artificial pump and artificial sphincter.

Another approach for limiting the axial movement of the plug, while permitting continued rotation of the driven magnet, is to use a screw and nut combination where one (or both) is at least partially flexible. When the axial force on the screw is above a certain threshold, the screw thread will start to disengage from the nut thread. Thus, when the plug is completely closed or opened, the screw could continue rotating without driving the nut axially.

It will also be appreciated that the implantable driven magnet can have a larger number of poles than that of the external drive magnet so as to be rotatable by the external drive magnet at a smaller angular velocity than the external drive magnet but with an increased torque ratio. Alternatively, the implantable driven magnet can have a smaller number of poles than that of the external magnet so as to be rotatable by the external drive magnet at a larger angular velocity than the external drive magnet.

Figure 20:
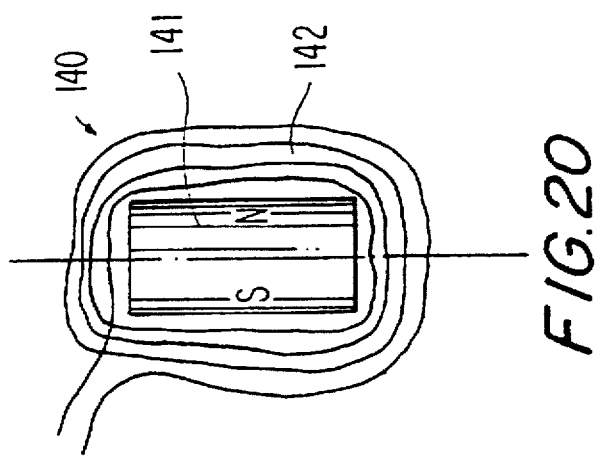
FIG. 20 illustrates the invention embodied in an implantable electrical generator for recharging an implanted battery.

FIG. 20 illustrates a further application of the invention wherein the device to be implanted is a generator, generally designated 140, enclosing the driven magnet 141. Thus, when magnet 141 is rotated, a voltage is generated within winding 142 to recharge a battery implanted within the subject's body, e.g., for powering an electrical device such as a pacemaker. Such an implanted generator can be driven by an external drive magnet in the same manner as described with respect to the other implementations of the invention and thus enables an implanted battery to be periodically recharged. The voltage generated by such a generator can also be used to generate heat at a desired region, or to directly drive an electric motor implanted within the subject's body.

Figure 21:
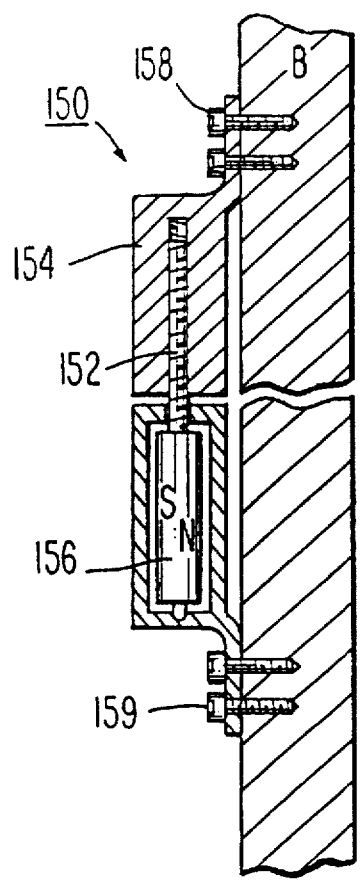
FIG. 21 illustrates the invention embodied in an implantable bone-stretching device.

FIG. 21 illustrates a still further application of the invention, wherein the device to be implanted is a bone-stretching device. Such a device includes a linearly-expansible assembly of a screw 152 threadedly received within a nut 154. The implanted driven magnet 156 is fixed to the screw 152, such that when the magnet is rotated, the screw moves nut 154 linearly away from the magnet. Opposite ends of assembly 150 are fixed by fasteners 158 and 159 to spaced locations of the bone B to be stretched. It will thus be seen that when magnet 156 is rotated by an external drive magnet in the same manner described above, this will rotate screw 152 and thereby move nut 154 axially away from the screw, such as to provide a tensile force to the bone B to stretch the bone.

While the invention has been described with respect to several preferred embodiments, it will be appreciated that these are set forth merely for purposes of example, and that many other variations, modifications and applications of the invention may be made.

I claim:

1. A medical apparatus, comprising:
   a drive magnet, externally located with respect to a subject's body, having a first axis, and mounted on a first support means for supporting said drive magnet along said first axis for rotation of said drive magnet about said first axis; and,
   an implant device implantable in the subject's body, said implant device comprising a valve and a pump, said valve having a fluid inlet and outlet for passage of fluid through said valve;
   said implant device further comprising a driven magnet having a second axis, said driven magnet being mounted on a second support means for supporting rotation of said driven magnet about said second axis by magnetic pole coupling with said drive magnet when said driven magnet is implanted in the subject's body and said drive magnet is rotated sufficiently close to said driven magnet to be magnetically coupled thereto; and,
   said valve being mechanically linked to the rotation of said driven magnet such that said valve is selectively opened and closed by rotation of said driven magnet.

2. The apparatus according to claim 1, wherein said implant device is dimensioned to be contained in a fluid carrying vessel in the subject's body.

3. The apparatus according to claim 2, wherein said fluid carrying vessel is the urethra.

4. The apparatus according to claim 1, wherein said valve comprises: a housing containing said driven magnet, a plug means, and a screw and nut motion converter means for axially displacing said plug means toward and away from said outlet, said screw and nut motion converter means being coupled to said plug means and to said second support means of said driven magnet so that said plug means is axially displaceable towards said outlet upon rotation of said driven magnet in a first direction and is axially displaceable away from said outlet upon rotation of said driven magnet in a second direction.

5. The apparatus according to claim 4, wherein said screw and nut motion converter means comprises a screw and a nut, and wherein said nut is fixed in relation to said housing and said plug means is axially displaceable with respect to said outlet by rotation of said screw within said nut.

6. The apparatus according to claim 4, wherein said screw and nut motion converter means comprises a screw and a nut, and wherein said nut is axially displaceable by rotation of said screw, and said nut carries said plug means.

7. The apparatus according to claim 1, wherein said valve is provided with pressure-sensitive opening means to release urine through said valve at a predetermined pressure threshold.

8. The apparatus according to claim 1, wherein said valve comprises a housing containing said driven magnet; a pivotal valve member having an open and a closed position, located at said outlet; and a screw and nut motion converter connected to said valve member so as to pivot said valve member to said open position upon the rotation of said driven magnet in a first direction, and to pivot said valve member to said closed position, upon rotation of said driven magnet in a second direction, opposite to said first direction.

9. The apparatus according to claim 8, wherein said valve is provided with pressure-sensitive opening means to release urine through said valve at a predetermined pressure threshold.

10. The apparatus according to claim 1, wherein said drive magnet and said driven magnet are each provided with more than two magnetic poles.

11. The apparatus according to claim 1, wherein said drive magnet and said driven magnet are different in size.

12. The apparatus according to claim 1, wherein said pump further comprises at least one stationary guide vane.

13. The apparatus according to claim 1, wherein said pump is mechanically coupled to said valve by a coupling means which permits said pump to continue pumping fluid by rotation of said driven magnet even after said valve has been moved to an open position.

14. The apparatus according to claim 13, wherein said coupling means comprises a threaded nut and a partially threaded screw.

15. A medical apparatus, comprising:
   a drive magnet, externally located with respect to a subject's body, having a first axis and mounted on a first support means for supporting said drive magnet along said first axis for rotation about said first axis;
   an implant device implantable in the subject's body, said implant device comprising a driven magnet having a second axis, said driven magnet being implantable in the subject's body and mounted on a second support means for supporting rotation of said driven magnet along said second axis by magnetic pole coupling with said drive magnet when said driven magnet is implanted in the subject's body and said drive magnet is rotated sufficiently close to said driven magnet to be magnetically coupled thereto;
   said implant device further comprising a valve, said valve having a fluid inlet and outlet for passage of fluid through said valve, said valve being mechanically linked to the rotation of said driven magnet such that said valve is selectively opened and closed by rotation of said driven magnet; and,
   said valve further comprising a plug means, and a screw and nut motion converter means for axially displacing said plug means toward and away from said outlet, said screw and nut motion converter means connected to said plug means and to said second support means of said driven magnet so that said plug means is axially displaceable towards said outlet upon rotation of said driven magnet in a first direction and is axially displaceable away from said outlet upon rotation of said driven magnet in a second direction.

16. The apparatus according to claim 15, wherein said implant device is configured and dimensioned to be contained in a fluid carrying vessel in the subject's body.

17. The apparatus according to claim 16, wherein said fluid carrying vessel is the urethra.

18. The apparatus according to claim 17, further comprising a pump.

19. The apparatus according to claim 17, wherein said driven magnet is contained in a housing, said housing comprising a tube dimensioned to be contained in a fluid carrying vessel of the subject's body.

20. The apparatus according to claim 15, wherein driven magnet is contained in a housing and said screw and nut motion converter means comprises a screw and a nut, said nut being fixed in relation to said housing and said plug means being axially displaceable with respect to said outlet by rotation of said screw within said nut.

21. The apparatus according to claim 15, wherein said screw and nut motion converter means comprises a screw and a nut, and wherein said nut is axially displaceable by rotation of said screw, and said nut carries said plug means.

22. The apparatus according to claim 15, wherein said valve is provided with pressure-sensitive opening means to release urine through said valve at a predetermined pressure threshold.

23. The apparatus according to claim 15, wherein said drive magnet and said driven magnet are each provided with more than two magnetic poles.

24. The apparatus according to claim 15, wherein said drive magnet and said driven magnet are different in size.

25. A medical apparatus, comprising:
a drive magnet, externally located with respect to a subject's body, having a first axis and mounted on a first support means for supporting said drive magnet along said first axis for rotation about said first axis; and, an implant device implantable in the subjects body, said implant device comprising a driven magnet, said driven magnet having a second axis and being mounted on a second support means for supporting rotation of said driven magnet along said second axis by magnetic pole coupling with said drive magnet when said driven magnet is implanted in the subject's body and said drive magnet is rotated sufficiently close to said driven magnet to be magnetically coupled thereto;

said implant device comprising a valve, said valve having a fluid inlet and outlet for passage of fluid through said valve, said valve being mechanically linked to the rotation of said driven magnet such that said valve is selectively opened and closed by rotation of said driven magnet, said valve comprises a housing containing said driven magnet, a pivotal valve member having an open and a closed position, located at said outlet; and a screw and nut motion converter means connected to said valve member so as to pivot said valve member to said open position upon the rotation of said driven magnet in a first direction, and to pivot said valve member to said closed position upon rotation of said driven magnet in the opposite direction.

26. The apparatus according to claim 25, wherein said implant device is dimensioned to be contained in a fluid carrying vessel in the subject's body.

27. The apparatus according to claim 25, wherein said implant device is dimensioned to be contained in the urethra.

28. The apparatus according to claim 27, wherein said housing comprises a tube.

29. The apparatus according to claim 25, wherein said screw and nut motion converter means comprises a screw and a nut, and wherein said nut is fixed in relation to said housing and said plug means is axially displaceable with respect to said outlet by rotation of said screw within said nut.

30. The apparatus according to claim 25, wherein said screw and nut motion converter means comprises a screw and a nut, and wherein said nut is axially displaceable by rotation of said screw, and said nut carries said plug means.

31. The apparatus according to claim 25, wherein said drive magnet and said driven magnet are each provided with more than two magnetic poles.

32. The apparatus according to claim 25, wherein said drive magnet and said driven magnet are different in size.

33. The apparatus according to claim 25, further comprising a pump having at least one stationary guide vane.

34. The apparatus according to claim 25, wherein said valve is provided with pressure-sensitive opening means to release urine through said valve at a predetermined pressure threshold.

35. A medical apparatus, comprising:
a drive magnet, externally located with respect to a subject's body, having a first axis, and mounted on a first support means for supporting said drive magnet along said first axis for rotation about said first axis; and, a fluid pump dimensioned to be contained in a fluid carrying vessel of the subject's body, said pump comprising a housing containing a driven magnet, an inlet and an outlet, said driven magnet having a second axis and being mounted on a second support means for supporting rotation of said driven magnet about said second axis by magnetic pole coupling with said drive magnet when said driven magnet is implanted in the subject's body and said drive magnet is rotated sufficiently close to said driven magnet to be magnetically coupled thereto.

36. The apparatus according to claim 35, wherein said pump is dimensioned to be contained in the urethra.

37. The apparatus according to claim 36, further comprising a valve, said valve comprising a plug means, and a screw and nut motion converter means for axially displacing said plug means toward and away from said outlet, said screw and nut motion converter means being coupled to said plug means and to said second support means of said driven magnet so that said plug means is axially displaceable towards said outlet upon rotation of said driven magnet in a first direction and is axially displaceable away from said outlet upon rotation of said driven magnet in a second, opposite direction.

38. The apparatus according to claim 37, wherein said driven magnet is contained in a housing, and wherein said screw and nut motion converter means comprises a screw and a nut, said nut being fixed in relation to said housing and said plug means being axially displaceable with respect to said outlet by rotation of said screw within said nut.

39. The apparatus according to claim 37, wherein said screw and nut motion converter means comprises a screw and a nut, and wherein said nut is axially displaceable by rotation of said screw, and said nut carries said plug means.

40. The apparatus according to claim 37, wherein said valve is further provided with pressure-sensitive opening means to release urine through said valve at a predetermined pressure threshold.

41. The apparatus according to claim 37, wherein said pump is coupled to said valve by a coupling means for permitting said pump to continue pumping fluid even after said valve has been moved to its open position.

42. The apparatus according to claim 36, further comprising a valve, said valve comprising a housing containing said driven magnet; a pivotal valve member having an open and a closed position, located at said outlet; and a screw and nut motion converter connected to said valve member so as to pivot said valve member to said open position upon the rotation of said driven magnet in a first direction, and to pivot said valve member to said closed position, upon rotation of said driven magnet in the opposite direction.

43. The apparatus according to claim 42, wherein said valve is provided with pressure sensitive opening means to release urine through said valve at a predetermined pressure threshold.

44. The apparatus according to claim 42, wherein said pump is coupled to said valve by a coupling means for permitting said pump to continue pumping fluid even after said valve has been moved to an open position.

45. The apparatus according to claim 44, wherein said coupling means comprises a threaded nut and a partially threaded screw.

46. The apparatus according to claim 36, wherein said drive magnet and said driven magnet are each provided with more than two magnetic poles.

47. The apparatus according to claim 36, wherein said drive magnet and said driven magnet are different in size.

48. The apparatus according to claim 36, wherein said pump further comprises at least one stationary guide vane.

49. A medical apparatus, comprising:

a drive magnet, externally located with respect to a subject's body, having a first axis and mounted on a first support means for supporting said drive magnet along said first axis for rotation about said first axis; and, a pump implantable in the subject's body, said pump comprising a tubular housing containing a driven magnet;

said driven magnet having a second axis and being mounted on a second support means contained in said housing for supporting rotation of said driven magnet about said second axis by magnetic pole coupling with said drive magnet when said housing is implanted in the subject's body and said drive magnet is rotated sufficiently close to said driven magnet to be magnetically coupled thereto; and, said pump comprising at least one impeller vane on the surface of said driven magnet to pump liquid through said housing upon rotation of said drive magnet.

50. The apparatus according to claim 49, wherein said housing is dimensioned to be contained in a fluid carrying vessel in the subject's body.

51. The apparatus according to claim 49, wherein said housing is dimensioned to be contained in the urethra.

52. The apparatus according to claim 49, wherein said housing further comprises a valve.

53. The apparatus according to claim 52, wherein said valve comprises a fluid inlet and outlet for passage of fluid through said valve, a plug means, and a screw and nut motion converter means for axially displacing said plug means toward and away from said outlet, said screw and nut motion converter means connected to said plug means and to said second support means of said driven magnet so that said plug means is axially displaceable towards said outlet upon rotation of said driven magnet in a first direction and is axially displaceable away from said outlet upon rotation of said driven magnet in a second, opposite direction.

54. The apparatus according to claim 52, wherein said valve comprises a fluid inlet and outlet for passage of fluid through said valve, said valve further comprising a pivotal valve member having an open and a closed position and located at said outlet, and a screw and nut motion converter means connected to said valve member so as to pivot said valve member to said open position upon the rotation of said driven magnet in a first direction, and to pivot said valve member to said closed position upon rotation of said driven magnet in a second, opposite direction.

55. The apparatus according to claim 52, wherein said valve is provided with pressure-sensitive opening means to release urine through said valve at a predetermined pressure threshold.

56. The apparatus according to claim 52, wherein said pump is mechanically coupled to said valve by a coupling means which permits said pump to continue pumping fluid even after said valve has been moved to an open position.

57. The apparatus according to claim 56, wherein said coupling means comprises a threaded nut and a partially threaded screw.

58. A medical apparatus, comprising:

a drive magnet, externally located with respect to a subject's body, having a first axis and mounted on a first support means for supporting said drive magnet along said first axis for rotation about said first axis; and a pump comprising a housing dimensioned to be contained in a fluid carrying vessel in the subject's body;

said housing containing a driven magnet, said driven magnet having a second axis and being mounted on a second support means in said housing for supporting rotation of said driven magnet about said second axis by magnetic pole coupling with said drive magnet when said driven magnet is implanted in the subject's body and said drive magnet is rotated sufficiently close to said driven magnet to be magnetically coupled thereto; and, said pump comprising at least one impeller vane on the surface of said driven magnet to pump liquid through said housing upon rotation of said drive magnet.

59. The apparatus according to claim 58, wherein said pump is configured and dimensioned to be contained in a fluid carrying vessel in the subject's body for pumping fluid in said vessel upon rotation of said drive magnet.

60. The apparatus according to claim 59, wherein said fluid carrying vessel is the urethra.

61. The apparatus according to claim 60, wherein said housing further comprises a valve.

62. The apparatus according to claim 61, wherein said valve comprises a fluid inlet and outlet for passage of fluid through said valve, a plug means, and a screw and nut motion converter means for axially displacing said plug means toward and away from said outlet, said screw and nut motion converter means connected to said plug means and to said second support means of said driven magnet so that said plug means is axially displaceable towards said outlet upon rotation of said driven magnet in a first direction and is axially displaceable away from said outlet upon rotation of said driven magnet in a second, opposite direction.

63. The apparatus according to claim 61, wherein said valve comprises a fluid inlet and outlet for passage of fluid through said valve, said valve further comprising a pivotal valve member having an open and a closed position and located at said outlet, and a screw and nut motion converter means connected to said valve member so as to pivot said valve member to said open position upon the rotation of said driven magnet in a first direction, and to pivot said valve member to said closed position upon rotation of said driven magnet in a second, opposite direction.

64. The apparatus according to claim 61, wherein said valve is provided with pressure-sensitive opening means to release urine through said valve at a predetermined pressure threshold.

65. The apparatus according to claim 61, wherein said pump is mechanically coupled to said valve by a coupling means which permits said pump to continue pumping fluid even after said valve has been moved to an open position.

66. The apparatus according to claim 65, wherein said coupling means comprises a threaded nut and a partially threaded screw.

67. A medical apparatus, comprising:

a drive magnet, externally located with respect to a subject's body, having a first axis and mounted on a first support means for supporting said drive magnet along said first axis for rotation about said first axis; and a pump implantable in the subject's body, said pump comprising a housing containing a driven magnet, said driven magnet having a second axis and being mounted on a second support means for supporting rotation of said driven magnet about said second axis by magnetic pole coupling with said drive magnet when said driven magnet is implanted in the subject's body and said drive magnet is rotated sufficiently close to said driven magnet to be magnetically coupled thereto;

said pump comprising at least one impeller vane on the surface of said driven magnet to pump liquid through said housing upon rotation of said drive magnet, and further comprising at least one stationary guide vane.

68. The apparatus according to claim 67, wherein said pump is configured and dimensioned to be contained in a fluid carrying vessel in the subject's body for pumping a fluid in said vessel upon rotation of said drive magnet.

69. The apparatus according to claim 68, wherein said fluid carrying vessel is the urethra.

70. The apparatus according to claim 69, wherein said housing further comprises a valve.

71. The apparatus according to claim 70, wherein said valve comprises a fluid inlet and outlet for passage of fluid through said valve, a plug means, and a screw and nut motion converter means for axially displacing said plug means toward and away from said outlet, said screw and nut motion converter means connected to said plug means and to said second support means of said driven magnet so that said plug means is axially displaceable towards said outlet upon rotation of said driven magnet in a first direction and is axially displaceable away from said outlet upon rotation of said driven magnet in a second, opposite direction.

72. The apparatus according to claim 70, wherein said valve comprises a fluid inlet and outlet for passage of fluid through said valve, said valve further comprising a pivotal valve member having an open and a closed position and located at said outlet, and a screw and nut motion converter means connected to said valve member so as to pivot said valve member to said open position upon the rotation of said driven magnet in a first direction, and to pivot said valve member to said closed position upon rotation of said driven magnet in a second, opposite direction.

73. The apparatus according to claim 70, wherein said valve is provided with pressure-sensitive opening means to release urine through said valve at a predetermined pressure threshold.

74. The apparatus according to claim 73, wherein said pump is mechanically coupled to said valve by a coupling means which permits said pump to continue pumping fluid even after said valve has been moved to an open position.

75. The apparatus according to claim 74, wherein said coupling means comprises a threaded nut and a partially threaded screw.

76. The apparatus according to claim 70, wherein said pump is mechanically coupled to said valve by a coupling means which permits said pump to continue pumping fluid even after said valve has been moved to an open position.

* * * * *